(12) United States Patent
Lee

(10) Patent No.: US 11,175,069 B2
(45) Date of Patent: Nov. 16, 2021

(54) AIR PURIFICATION-AROMATHERAPY MACHINE

(71) Applicant: PUZHEN LIFE CO., LTD., Shatin (HK)

(72) Inventor: Andy Lee, Shatin (HK)

(73) Assignee: Puzhen Life Co., LTD., Shatin (HK)

( * ) Notice: Subject to any disclaimer, the term of this patent is extended or adjusted under 35 U.S.C. 154(b) by 71 days.

(21) Appl. No.: 16/805,843

(22) Filed: Mar. 2, 2020

(65) Prior Publication Data

US 2021/0180827 A1   Jun. 17, 2021

(30) Foreign Application Priority Data

Dec. 17, 2019   (CN) .......................... 201922272553.3

(51) Int. Cl.
| | | |
|---|---|---|
| *F24F 1/00* | (2019.01) | |
| *F24F 13/24* | (2006.01) | |
| *B01F 3/04* | (2006.01) | |
| *B01D 46/00* | (2006.01) | |
| *B01D 29/00* | (2006.01) | |
| *B01D 46/42* | (2006.01) | |
| *F24F 1/0073* | (2019.01) | |
| *F24F 1/008* | (2019.01) | |
| *A61L 9/14* | (2006.01) | |

(52) U.S. Cl.
CPC ................ *F24F 13/24* (2013.01); *A61L 9/14* (2013.01); *B01D 29/0018* (2013.01); *B01D 46/0038* (2013.01); *B01D 46/4236* (2013.01); *B01F 3/04* (2013.01); *F24F 1/008* (2019.02); *F24F 1/0073* (2019.02); *F24F 2013/242* (2013.01)

(58) Field of Classification Search
CPC ............ B01D 46/4236; B01D 46/0038; B01D 29/0018; B01F 3/04; F24F 13/24; F24F 1/008

See application file for complete search history.

(56) References Cited

U.S. PATENT DOCUMENTS 10,967,092 B2 *   4/2021   Chang ................. B01F 3/04021

FOREIGN PATENT DOCUMENTS

CN          209355392 U  *  9/2019  ................ F24F 3/16

* cited by examiner

*Primary Examiner* — Robert A Hopkins
(74) *Attorney, Agent, or Firm* — Robert L. Stearns; Dickinson Wright, PLLC

(57) ABSTRACT

An air purification-aromatherapy machine includes a housing, an aromatherapy assembly, a filter screen, and an air extractor; the housing is provided with an air inlet and an air outlet; the aromatherapy assembly, the filter screen and the air extractor are placed in the housing; the air extractor comprises a fan, an air duct configured for guiding an airflow blown by the fan to the air outlet, and a sound absorber configured for absorbing noise of the airflow; an end of the air duct is extended to the air outlet, the sound absorber is placed in the air duct and corresponding to the air outlet.

14 Claims, 6 Drawing Sheets

AIR PURIFICATION-AROMATHERAPY MACHINE

CROSS REFERENCE TO RELATED APPLICATION

The present application claims priority to Chinese Patent Application Ser. No. CN201922272553.3, filed on Dec. 17, 2019, the entire content of which is incorporated herein by reference.

TECHNICAL FIELD

The present application relates to the technical field of air purification, and more particularly to an air purification-aromatherapy machine.

BACKGROUND

With the continuous improvement of people's living standards, more and more users use incense-type air purifiers to purify and incense indoor air to improve indoor air quality. At present, an incense-type air purifier is generally provided with an incense box in a box of the air purifier. Since the incense box is placed in the box of the air purifier, it is necessary to rely on the high-speed operation of the fan to improve the flow of airflow, so that the incense air in the incense box can be discharged into the indoor air. This will cause a larger noise when the air purifier is working, especially when the air purifier is operated at night, and it will affect the user's sleep and rest.

SUMMARY

An object of the present application is to provide an air purification-aromatherapy machine, so as to solve the problem in the art that the incense-type air purifier will cause a larger noise when operated.

In order to achieve above object, the present application adopt the technical solution is to provide an air purification-aromatherapy machine, including:

a housing, defining therein an air inlet and an air outlet;

an aromatherapy assembly, placed in the housing and configured to diffuse an essential oil for aromatherapy;

a filter screen, disposed in the housing and configured for purifying air in the housing; and an air extractor, arranged in the housing;

the air extractor comprises a fan, an air duct configured for guiding an airflow blown by the fan to the air outlet, and a sound absorber configured for absorbing noise of the airflow; an end of the air duct is extended to the air outlet, the sound absorber is placed inside the air duct corresponding to the air outlet, the sound absorber is configured to block the air outlet to form a ring-shaped air outlet port, the fan is placed inside the air duct, and the housing is provided with an aerosol exit orifice configured for spreading the diffused essential oil to an outward of the housing.

In an embodiment, an external contour of the sound absorber is in a bowl shape, a smaller diameter end of the sound absorber is extended into the air duct, and a larger diameter end of the sound absorber is located at a position of the air duct adjacent to the air outlet.

In an embodiment, an end of the air duct adjacent to the air outlet is provided with a tapered pipe section, an inner diameter of the tapered pipe section gradually decreasing toward the air outlet, and the sound absorber being placed in the tapered pipe section.

In an embodiment, the filter screen is located at the air inlet.

In an embodiment, the filter screen is a foldable filter screen.

In an embodiment, the fan comprises an impeller and a driving motor configured for driving the impeller to rotate.

In an embodiment, the aromatherapy assembly includes an essential oil bottle configured for storing the essential oil, and an atomizing device configured for atomizing the essential oil in the essential oil bottle and spraying the atomized essential oil out, and the essential oil bottle and the atomizing device are placed in the housing.

In an embodiment, the atomizing device includes an air pump configured for providing an airflow, an atomizing cover provided with an atomizing cavity, and an air spraying nozzle placed in the atomizing cavity, an air pipe connecting the air pump and the air spraying nozzle, an oil suction pipe extending into the essential oil bottle, and an oil spraying nozzle connected to the oil suction pipe; the atomizing cover is provided with a connection port configured for fittingly connecting with the essential oil bottle, the connection port is in communication with the atomizing cavity, an air outlet of the air spraying nozzle is located at a position corresponding to an oil outlet of the oil spraying nozzle, and the atomizing cavity is in communication with the aerosol exit orifice.

In an embodiment, an outer sidewall of a bottleneck of the essential oil bottle is provided with an external thread, and an inner sidewall of the connection port is provided with an internal thread corresponding to the external thread.

In an embodiment, the air inlet is provided therein with an air inlet grill configured for diffusing the airflow.

The one or more technical solutions in the embodiments of the present application have at least one of the following technical effects:

The beneficial effect of the air purification-aromatherapy machine provided by the present application is that, compared with the prior art, in the air purification-aromatherapy machine of the present application, and the air duct is disposed in the housing, the fan is placed in the air duct. When in use, the airflow blown by the fan is guided to the air outlet through the air duct to avoid agitated turbulence of the airflow in the housing and reduce the noise generated when the airflow flows. In addition, the sound absorber is provided at the corresponding air outlet in the air duct, during the process of the airflow in the housing discharging from the ring-shaped air outlet port, the sound absorber absorbs the noise of the airflow, which further reduces the generation of noise and avoids the air purification-aromatherapy machine to produce a larger noise during work.

BRIEF DESCRIPTION OF THE DRAWINGS

In order to explain the embodiments of the present application more clearly, a brief introduction regarding the accompanying drawings that need to be used for describing the embodiments of the present application or the prior art is given below; it is obvious that the accompanying drawings described as follows are only some embodiments of the present application, for those skilled in the art, other drawings can also be obtained according to the current drawings on the premise of paying no creative labor.

Figure 1:
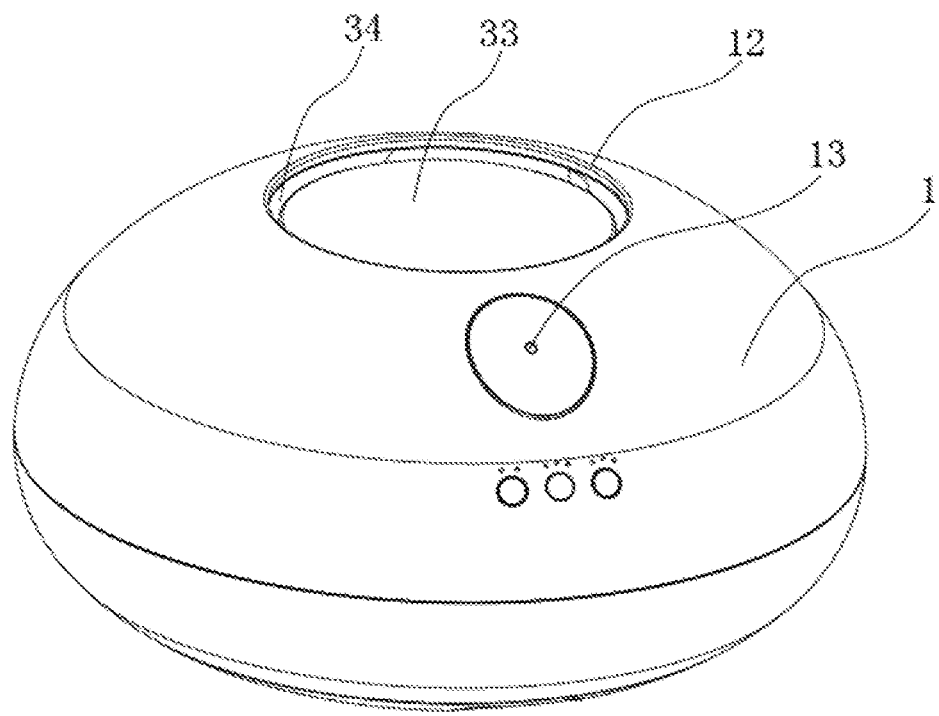
FIG. 1 is a first schematic view of a perspective structure of an air purification-aromatherapy machine provided by an embodiment of the present application.

In the drawings, the numerals referring to the technical features are listed as follows:

1-housing; 11-air inlet; 12-air outlet; 13-aerosol exit orifice; 14-air inlet grill;

2-aromatherapy assembly; 21-essential oil bottle; 22-atomizing device; 221-air pump; 222-atomizing cover; 223-atomizing cavity; 224-air spraying nozzle; 225-oil spraying nozzle; 226-connection port; 227-oil suction pipe;

3-air extractor; 31-air duct; 311-tapered pipe section; 32-fan; 321-impeller; 322-driving motor; 33-sound absorber; 34-ring-shaped air outlet port; and 4-filter screen.

DETAILED DESCRIPTION

In order to make the purpose, the technical solution and the advantages of the present application be clearer and more understandable, the present application will be further described in detail below with reference to accompanying figures and embodiments. It should be understood that the specific embodiments described herein are merely intended to illustrate but not to limit the present application.

It is noted that when a component is referred to as being "fixed to" or "disposed on" another component, it can be directly or indirectly on another component. When a component is referred to as being "connected to" another component, it can be directly or indirectly connected to another component.

It needs to be understood that, terms "the first" and "the second" are only used in describe purposes, and should not be considered as indicating or implying any relative importance, or impliedly indicating the number of indicated technical features. As such, technical feature(s) restricted by "the first" or "the second" can explicitly or impliedly comprise one or more such technical feature(s). In the description of the present application, "a plurality of" means two or more, unless there is additional explicit and specific limitation.

In the description of the present application, it should be noted that the terms "installation", "connecting", and "connected" should be understood in a broad sense, unless explicitly stated and limited otherwise. For example, they may be fixed connections or removable, or integrated; it can be mechanically connected or electrically connected; it can be directly connected or indirectly connected through an intermediate medium; it can be the internal connection of two elements or the interaction between two elements. For those of ordinary skill in the art, the specific meanings of the above terms in the present application can be understood according to specific situations.

Please refer to FIG. 1, FIG. 2 and FIG. 3 together, and the air purification-aromatherapy machine provided in the present application will now be described. The air purification-aromatherapy machine provided in this application includes a housing 1, an aromatherapy assembly 2, a filter screen 4, and an air extractor 3. The housing 1 is provided with an air inlet 11 and an air outlet 12, and the aromatherapy assembly 2 is placed in the housing 1 for the essential oil diffusing in the air to achieve the purpose of aromatherapy air. The filter screen 4 is located in the housing 1 and is configured to filter and purify the air in the housing 1. The air extractor 3 is located in the housing 1, and the air extractor 3 includes a fan 32, an air duct 31 for guiding the airflow blown by the fan 32 to the air outlet 12, and a sound absorber 33 configured for absorbing the noise of the airflow, an end of the air duct 31 extends to the air outlet 12, and the sound absorber 33 is placed in the air duct 31 corresponding to the air outlet 12, and the sound absorber 33 blocks the air outlet 12 to form a ring-shaped air outlet port 34, and fan 32 is placed in the air duct 31, the housing 1 is provided with an aerosol exit orifice 13 for spreading the diffused essential oil to the outward of the housing 1.

Compared with the prior art, in the air purification-aromatherapy machine of the present application, and the air duct 31 is disposed in the housing 1, the fan 32 is placed in the air duct 31. When in use, the airflow blown by the fan 32 is guided to the air outlet 12 through the air duct 31 to avoid agitated turbulence of the airflow in the housing 1 and reduce the noise generated when the airflow flows. In addition, the sound absorber 33 is provided at the corresponding air outlet 12 in the air duct 31, during the process of the airflow in the housing 1 discharging from the ring-shaped air outlet port 34, the sound absorber 33 absorbs the noise of the airflow, which further reduces the generation of noise and avoids the air purification-aromatherapy machine to produce a larger noise during work. In addition, the sound absorber blocks the air outlet 12 to form the ring-shaped air outlet port 34. When the airflow in the housing 1 is discharged from the ring-shaped air outlet port 34, the area of the air outlet is reduced, and the airflow velocity is accelerated, which makes the purified air easier reaching the farthest place in the room and speeding up the circulation of air.

Specifically, the sound absorber 33 is made of sound-absorbing materials such as porous organic fibers, inorganic fibers, inorganic foams, and foam plastics having good sound-absorbing effects and reducing noise generated by airflow.

Specifically, the filter screen 4 may include, but is not limited to, an electrostatic electret filter screen with low wind resistance, high efficiency, and high dust holding capacity, an activated carbon filter with a developed void structure and a large surface area, or an efficient particulate air filter (HEPA filter).

Figure 3:
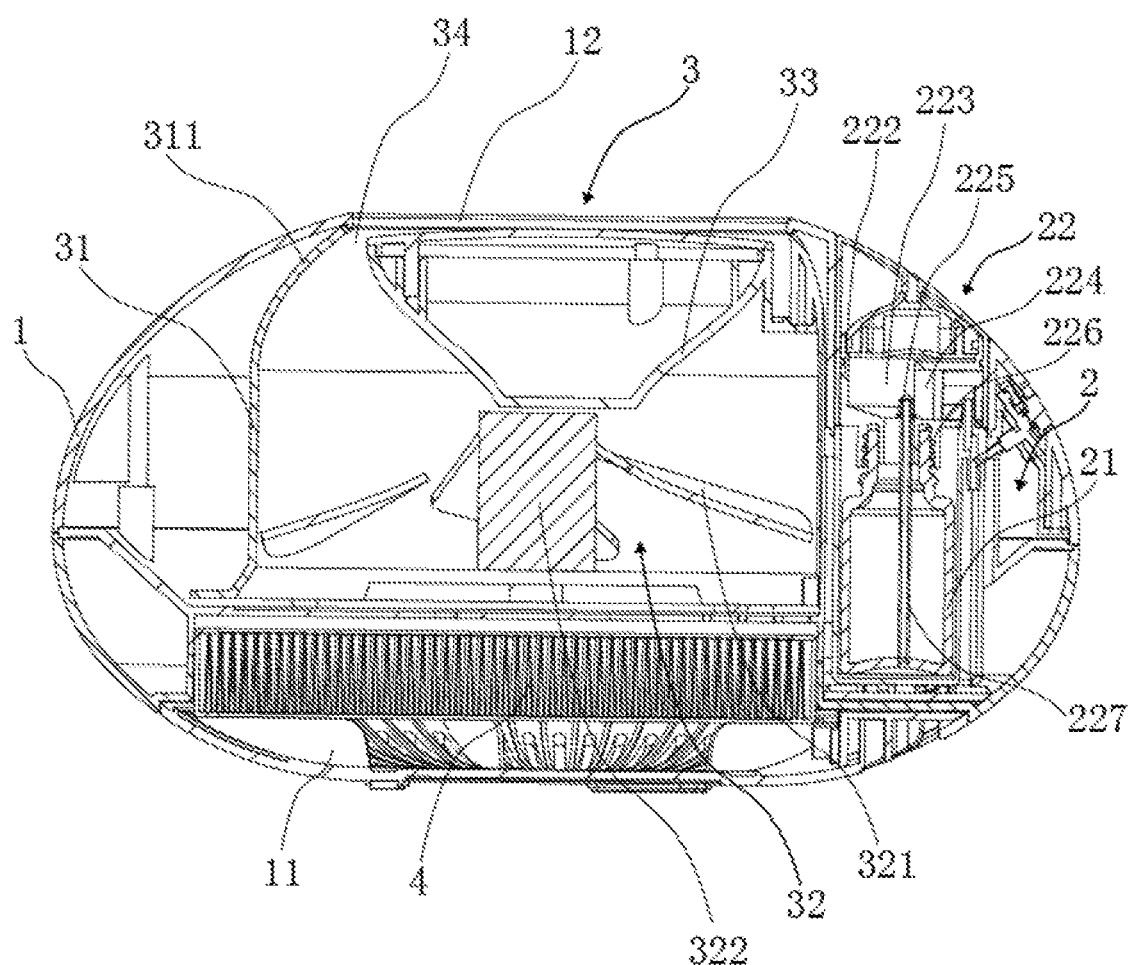
FIG. 3 is a schematic view of a cross-sectional structure of an air purification-aromatherapy machine provided by an embodiment of the present application.
Figure 4:
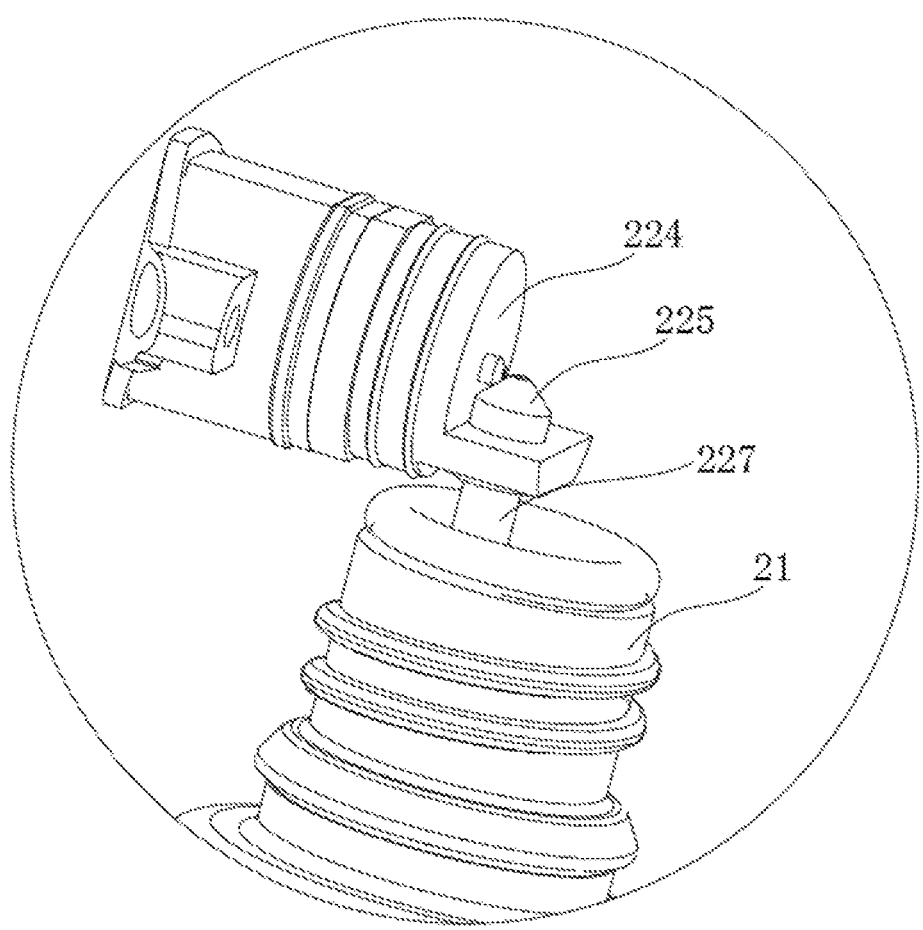
FIG. 4 is a schematic view of a partial enlarged structure of an air spraying nozzle provided by an embodiment of the present application.

In an embodiment, please refer to FIG. 3 and FIG. 4. As a specific implementation of the air purification-aromatherapy machine provided in the present application, the outer contour of the sound absorber 33 is in a bowl-shaped, and a smaller diameter end of the sound absorber 33 is extended into the air duct 31, and a larger diameter end of the sound absorber 33 is located at a position of the air duct 31 adjacent to the air outlet 12.

In this embodiment, a bowl-shaped sound absorber 33 is provided in the air duct 31 corresponding to the air outlet 12 and the smaller diameter end of the sound absorber 33 is inserted into the air duct 31, and the larger diameter end of the sound absorber 33 is located at a position of the air duct 31 adjacent to the air outlet 12, thereby when the air is concentratedly discharged from the air outlet 12, through the bowl-shaped sound absorber 33, it has the effect of diffusing the air from the center to the surroundings, the buffering effect reduces the velocity of the airflow, effectively avoiding the turbulence caused by the airflow agitation, thereby further reducing the noise. In addition, the bowl-shaped sound absorber 33 blocks the air outlet 12 to form the ring-shaped air outlet port 34, such that when the air flow is discharged from the ring-shaped air outlet port 34, the air velocity when the air flow is exhausted from housing 1 can be increased, and the circulation effect of the filtered and purified air can be higher.

Figure 6:
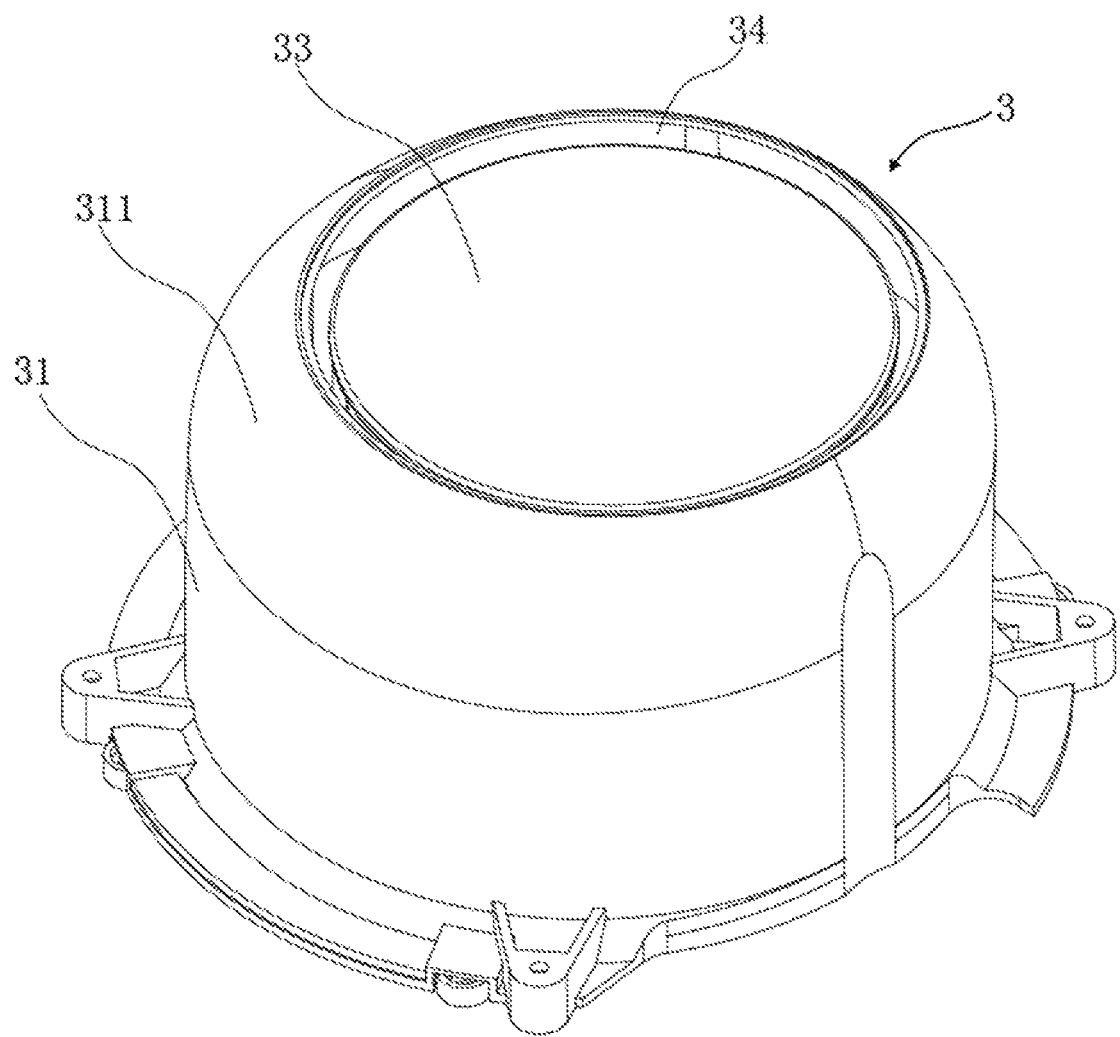
FIG. 6 is a perspective schematic view of an air extractor provided by an embodiment of the present application.

In an embodiment, please refer to FIG. 3 and FIG. 6. As a specific implementation of the air purification-aromatherapy machine provided in the present application, an end of the air duct 31 adjacent to the air outlet 12 is provided with a tapered pipe section 311, and the inner diameter of the tapered pipe section 311 gradually decreases toward the air outlet 12, and the sound absorber 33 is placed in the tapered pipe section 311.

In one embodiment, please refer to FIG. 3. As a specific implementation of the air purification-aromatherapy machine provided in the present application, the filter screen 4 is located at the air inlet 11 to reduce the wind resistance of the filter screen 4 to the airflow and increase the wind pressure, such that the air flow is fully in contact with filter screen 4 to improve the effect of air filtration and purification.

Figure 7:
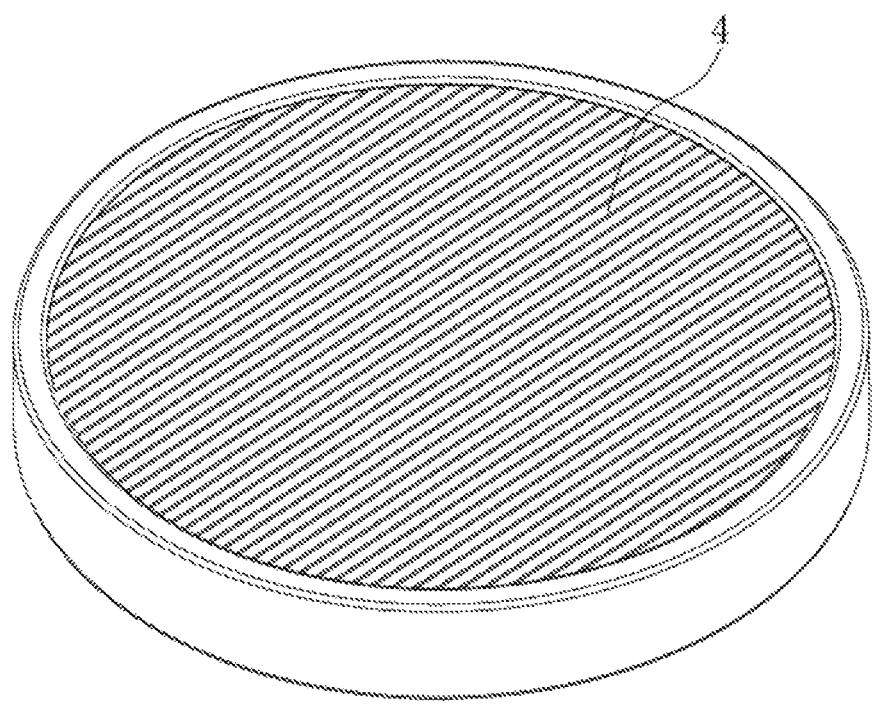
FIG. 7 is a perspective schematic view of a filter screen provided by an embodiment of the present application.

In one embodiment, please refer to FIG. 3 and FIG. 7. As a specific implementation of the air purification-aromatherapy machine provided in the present application, the filter screen 4 is a foldable filter set. In this embodiment, by setting the filter screen 4 as a foldable filter screen, the contact surface between the air flow and the filter screen 4 is increased, and the efficiency of air filtration and purification is improved.

Figure 5:
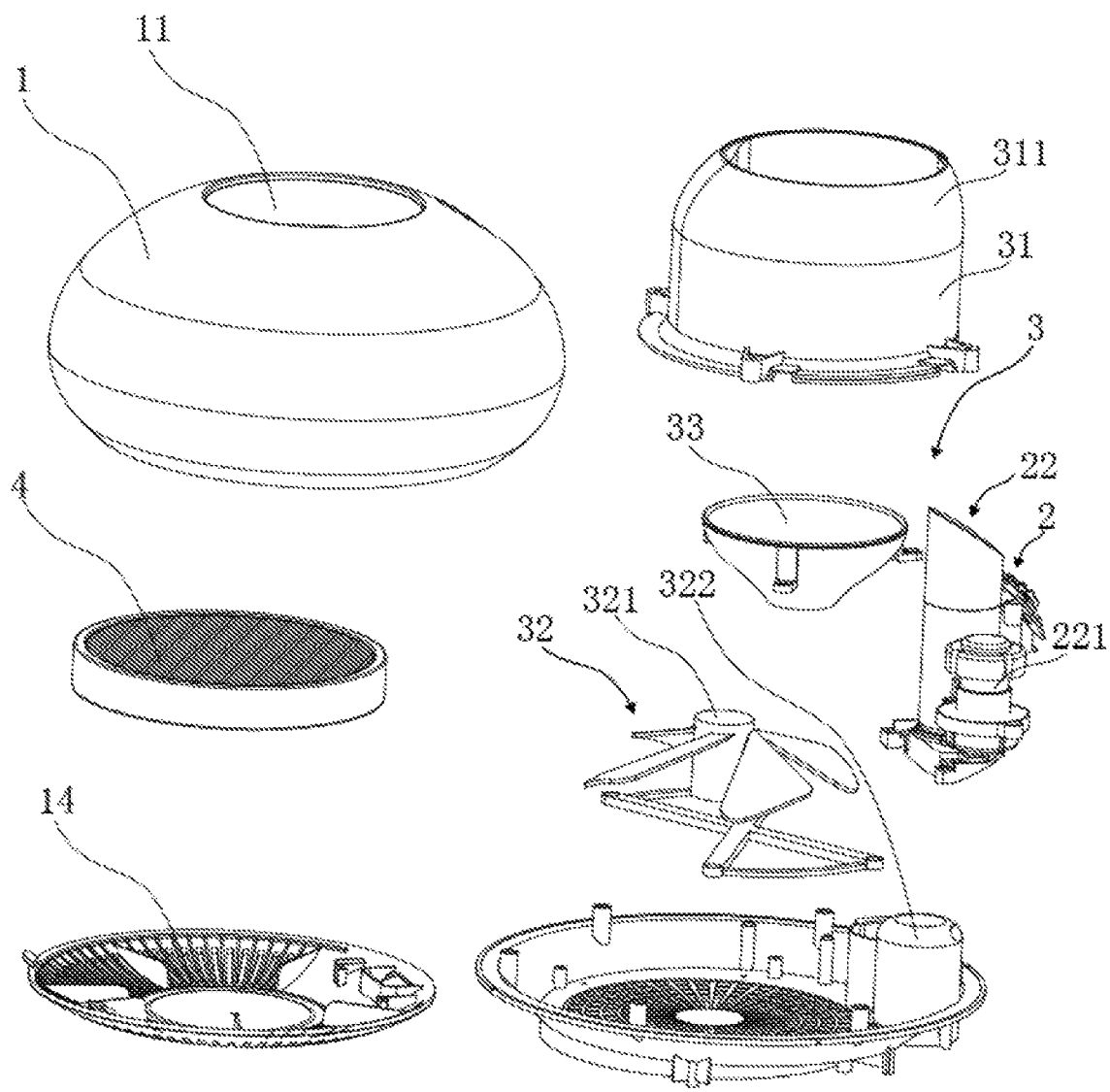
FIG. 5 is a schematic view of an explosion structure of an air purification-aromatherapy machine provided by an embodiment of the present application.

In an embodiment, please refer to FIG. 3 and FIG. 5. As a specific implementation of the air purification-aromatherapy machine provided in the present application, the fan 32 includes an impeller 321 and a driving motor 322 that drives the impeller 321 to rotate.

In this embodiment, the fan 32 is a centrifugal fan 32. The fan 32 includes an impeller 321 and a driving motor 322 that drives the impeller 321 to rotate. The driving motor 322 drives the impeller 321 to rotate to realize the centrifugal motion of the airflow, such that the negative pressure generated in the housing 1 causes a lager suction force of the airflow, which increases the wind pressure and is conducive to the rapid purification and purification of the airflow through the filter screen 4, and improves the filtration efficiency.

In an embodiment, please refer to FIG. 3, FIG. 4, and FIG. 5. As a specific implementation of the air purification-aromatherapy machine provided in the present application, the aromatherapy assembly 2 includes an essential oil bottle 21 configured for storing essential oils and an atomizing device 22 configured for atomizing the essential oils in the essential oil bottle 21 and spraying them out, and the essential oil bottle 21 and the atomizing device 22 are placed in the housing 1.

In the embodiment, the aromatherapy assembly 2 includes the essential oil bottle 21 and the atomizing device 22 that are placed in the housing 1. The essential oil can be stored in the essential oil bottle 21 in advance, and then the essential oils in the in essential oil bottle 21 are atomized to form mist-like essential oil particles by the atomizing device 22, and the mist-like essential oil particles are diffused into the air of the vehicle through the aerosol exit orifice 13 on the housing 1, which play a role of incense to the air of the vehicle.

In one embodiment, please refer to FIG. 3, FIG. 4, and FIG. 5. As a specific implementation of the air purification-aromatherapy machine provided in the present application, the atomizing device 22 includes an air pump 221 configured for providing airflow, an atomizing over 222 provided with an atomizing cavity 223, an air spraying nozzle 224 placed in the atomizing cavity 223, an air pipe (not shown in the figure) connecting the air pump 221 and the air spraying nozzle 224, an oil suction pipe 227 extending into essential oil bottle 21 and an oil spraying nozzle 225 connected to the oil suction pipe 227. The atomizing cover 222 is provided with a connection port 226 configured for fittingly connecting with the essential oil bottle 21, the connection port 226 is in communication with the atomizing cavity 223, and an air outlet of the air spraying nozzle 224 is located at a position corresponding to an oil outlet of the oil spraying nozzle 225, and the atomizing cavity 223 is in communication with the aerosol exit orifice 13.

In the embodiment, the atomizing over 222 is provided with the atomizing cavity 223, and the atomizing over 222 is provided with the aerosol exit orifice 13 which in communicates with the atomizing cavity 223. A lower end of the atomizing over 222 is provided with the connection port 226, and the bottle mouth of the essential oil bottle 21 is connected to the atomizing over 222 through the connection port 226. The atomizing over 222 is installed on the housing 1, and the air pump 221 is installed in the housing such that the housing 1 is configured to support and protect the air pump 221. An end of the air pipe is connected with the air pump 221, and the other end of the air pipe is connected to the air spraying nozzle 224, the airflow provided by the air pump 221 is transmitted to the air spraying nozzle 224 through the air pipe, and is sprayed from the air spraying nozzle 224. The oil outlet of the oil spraying nozzle 225 is located in the atomizing cavity 223, the air outlet of the air spraying nozzle 224 is located at the position corresponding to the oil outlet of the oil spraying nozzle 225, and the oil spraying nozzle 225 is located at the corresponding position of the connection port 226, such that the oil spraying nozzle 225 can extract essential oil from the essential oil bottle 21 through the oil suction pipe 227, when the connection port 226 is connected to the essential oil bottle 21, and the upper end of oil spraying nozzle 225 extends into atomizing cavity 223, and the outlet of air spraying nozzle 224 is located at the upper end of the oil spraying nozzle 225; when the air pump 221 generates a high-pressure gas and sprays them out from the air spraying nozzle 224, a negative pressure will be formed at the nozzle of the upper end of oil spraying nozzle 225, so as to extract essential oil from the essential oil bottle 21 through oil suction pipe 227 under the negative pressure, and the extracted essential oil is sprayed from the oil spraying nozzle of oil spraying nozzle 225, and the sprayed droplets will be scattered by the high-speed airflow sprayed from air spraying nozzle 224 to be atomized to form a mixed airflow, and the pressure in the atomizing cavity 223 is increased; and due to the connection of the connection port 226 and the essential oil bottle 21, the airflow in the atomizing cavity 223 is sprayed from aerosol exit orifice 13 to realize the aroma of the air in the car and achieve the purpose of improving the air quality in the vehicle.

In an embodiment, please refer to FIG. 3, an external thread is provided on an outer wall of a bottleneck of the essential oil bottle 21, and an internal thread matching the external thread is provided on an inner wall of the connection port 226.

Figure 2:
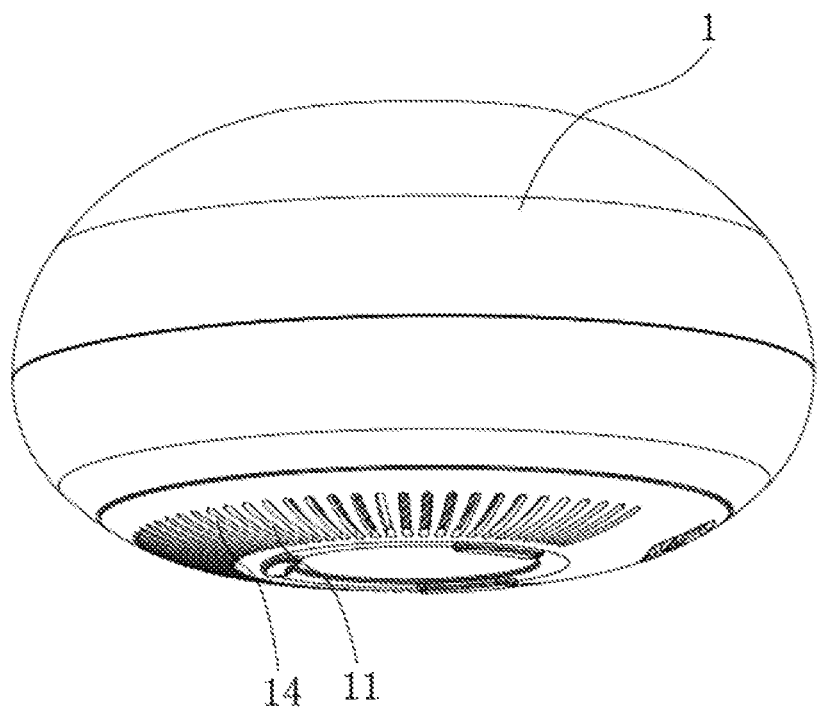
FIG. 2 is a second schematic view of a perspective structure of an air purification-aromatherapy machine provided by an embodiment of the present application.

In an embodiment, please refer to FIG. 2, FIG. 3 and FIG. 5. As a specific implementation of the air purification-aromatherapy machine provided in the present application, an air inlet grill 14 configured for dispersing airflow is provided in the air inlet 11. In this embodiment, the air inlet grill 14 is provided in the air inlet 11 to disperse the airflow through the air inlet grill 14 to prevent the airflow from flowing too concentratedly to the air purification cylinder, which may strongly impact the filter screen 4 of the air purification cylinder and affect the filtering effect.

In one embodiment, please refer to FIG. 3. As a specific implementation of the air purification-aromatherapy machine provided in the present application, the bottom of the atomizing cavity 223 has an inclined surface extending obliquely to the connection port 226.

In this embodiment, the bottom of the atomizing cavity 223 has the inclined surface extending obliquely to the connection port 226, with the guidance of the inclined surface, large particles of essential oil droplets are guided back to the essential oil bottle 21 to avoid affecting the effect of atomizing the essential oil and reducing the essential oil waste.

In an embodiment, please refer to FIG. 4. As a specific implementation of the air purification device provided in the present application, an end of the oil spraying nozzle 225 away from the oil outlet is provided with a connection sleeve, and the oil suction pipe 227 is detachably inserted in the connection sleeve, and the oil suction pipe 227 is placed in the essential oil bottle 21.

In the embodiment, the connection sleeve is provided at an end of the oil spraying nozzle 225 away from the oil outlet, and the oil suction pipe 227 is detachably inserted in the connection sleeve, and an oil suction pipe 227 is connected to the lower end of the oil spraying nozzle 225, the essential oil in the essential oil bottle 21 is sucked to the oil spraying nozzle 225 by the oil suction pipe 227 under the action of a negative pressure. In addition, the oil suction pipe 227 is detachably inserted into the connection sleeve of the oil spraying nozzle 225, and the oil suction pipe 227 of different length can be replaced according to different essential oil bottle 21 to improve the adaptability.

In an embodiment, please refer to FIG. 3. As a specific implementation of the air purification-aromatherapy assembly 2 provided in the present application, the housing 1 is provided with an accommodating bin configured for accommodating and positioning the essential oil bottle 21, so as to accommodate and position the essential oil bottle 21 in the housing 1, which facilitates the installation of the essential oil bottle 21 and enhances the stability of installation of the essential oil bottle 21.

In an embodiment, please refer to FIG. 4. As a specific implementation of the air purification-aromatherapy assembly 2 provided in the present application, the axial direction of the outlet of the air spraying nozzle 224 points to the top of the upper side wall of the oil spraying nozzle 225, such that when the air is sprayed from the outlet of the air spraying nozzle 224, the air can cover the upper end of the oil spraying nozzle 225 to better form a vacuum at the upper end of the oil spraying nozzle 225, in addition, the top of the upper sidewall of the oil spraying nozzle 225 can change the direction of airflow sprayed by the air spraying nozzle 224, which can better atomize the essential oil droplets extracted by oil spraying nozzle 225.

Furthermore, referring to FIG. 4, as a specific implementation of the air purification-aromatherapy assembly 2 provided in the present application, the axial direction of the outlet of the air spraying nozzle 224 is inclined upwardly to point to the top of the upper sidewall of the oil spraying nozzle 225. This structure can prevent the airflow sprayed by air spraying nozzle 224 from blowing into the nozzle at the upper end of oil spraying nozzle 225, so that the essential oil can be better extracted, and the extracted essential oil can be blown out obliquely upward, which can better atomize the essential oil.

In an embodiment, please refer to FIG. 4. As a specific implementation of the air purification-aromatherapy assembly 2 provided in the present application, the sidewall of the upper end of the oil spraying nozzle 225 is conical, so that the sidewall of the upper end of the oil spraying nozzle 225 is conical, the sidewall of the upper end of the oil spraying nozzle 225 can guide the airflow sprayed by the air spraying nozzle 224 upwardly, so that the airflow can better atomize the essential oil extracted by the oil spraying nozzle 225. In some other embodiments, the sidewall of the upper end of the oil spraying nozzle 225 may have a circular arc shape protruding upwardly.

The aforementioned embodiments are only preferred embodiments of the present application. For one of ordinary skill in the art, according to the thought of the present application, specific implementation modes and application scopes may be modified, and the content of the specification should not be interpreted as any limitation to the present application.

What is claimed is:

1. An air purification-aromatherapy machine, comprising:
a housing, defining therein an air inlet and an air outlet;
an aromatherapy assembly, placed in the housing and configured to diffuse an essential oil for aromatherapy;
a filter screen, disposed in the housing and configured for purifying air in the housing; and
an air extractor, arranged in the housing;
wherein the air extractor comprises a fan, an air duct configured for guiding an airflow blown by the fan to the air outlet, and a sound absorber configured for absorbing noise of the airflow; wherein an end of the air duct is extended to the air outlet, the sound absorber is placed inside the air duct corresponding to the air outlet, the sound absorber is configured to block the air outlet to form a ring-shaped air outlet port, the fan is placed inside the air duct, and the housing is provided with an aerosol exit orifice configured for spreading the diffused essential oil to an outward of the housing;
wherein the aromatherapy assembly comprises an essential oil bottle configured for storing the essential oil, and an atomizing device configured for atomizing the essential oil in the essential oil bottle and spraying the atomized essential oil out, and the essential oil bottle and the atomizing device are placed in the housing; and
wherein the atomizing device comprises an air pump configured for providing an airflow, an atomizing cover provided with an atomizing cavity, and an air spraying nozzle placed in the atomizing cavity, an air pipe connecting the air pump and the air spraying nozzle, an oil suction pipe extending into the essential oil bottle, and an oil spraying nozzle connected to the oil suction pipe; wherein the atomizing cover is provided with a connection port configured for fittingly connecting with the essential oil bottle, the connection port is in communication with the atomizing cavity, an air outlet of the air spraying nozzle is located at a position corresponding to an oil outlet of the oil spraying nozzle, and the atomizing cavity is in communication with the aerosol exit orifice.

2. The air purification-aromatherapy machine of claim 1, wherein an external contour of the sound absorber is in a bowl shape, a smaller diameter end of the sound absorber is extended into the air duct, and a larger diameter end of the sound absorber is located at a position of the air duct adjacent to the air outlet.

3. The air purification-aromatherapy machine of claim 2, wherein an end of the air duct adjacent to the air outlet is provided with a tapered pipe section, an inner diameter of the tapered pipe section gradually decreasing toward the air outlet, and the sound absorber being placed in the tapered pipe section.

4. The air purification-aromatherapy machine of claim 1, wherein the filter screen is located at the air inlet.

5. The air purification-aromatherapy machine of claim 2, wherein the filter screen is a foldable filter screen.

6. The air purification-aromatherapy machine of claim 1, wherein the fan comprises an impeller and a driving motor configured for driving the impeller to rotate.

7. The air purification-aromatherapy machine of claim 1, wherein an outer sidewall of a bottleneck of the essential oil bottle is provided with an external thread, and an inner sidewall of the connection port is provided with an internal thread corresponding to the external thread.

8. The air purification-aromatherapy machine of claim 1, wherein the air inlet is provided therein with an air inlet grill configured for diffusing the airflow.

9. The air purification-aromatherapy machine of claim 2, wherein the air inlet is provided therein with an air inlet grill configured for diffusing the airflow.

10. The air purification-aromatherapy machine of claim 3, wherein the air inlet is provided therein with an air inlet grill configured for diffusing the airflow.

11. The air purification-aromatherapy machine of claim 4, wherein the air inlet is provided therein with an air inlet grill configured for diffusing the airflow.

12. The air purification-aromatherapy machine of claim 5, wherein the air inlet is provided therein with an air inlet grill configured for diffusing the airflow.

13. The air purification-aromatherapy machine of claim 6, wherein the air inlet is provided therein with an air inlet grill configured for diffusing the airflow.

14. The air purification-aromatherapy machine of claim 7, wherein the air inlet is provided therein with an air inlet grill configured for diffusing the airflow.

* * * * *